United States Patent [19]

Ara et al.

[11] Patent Number: 5,147,795
[45] Date of Patent: Sep. 15, 1992

[54] ALKALINE PULLULANASE FROM BACILLUS SP. FERM P-10887

[75] Inventors: Katsutoshi Ara, Oyama; Kazuaki Igarashi, Ichikai; Katsuhisa Saeki, Kawachi; Susumu Ito, Utsunomiya, all of Japan

[73] Assignee: Kao Corporation, Tokyo, Japan

[21] Appl. No.: 575,434

[22] Filed: Aug. 30, 1990

[30] Foreign Application Priority Data

Aug. 31, 1989 [JP] Japan ................... 1-226210
Aug. 31, 1989 [JP] Japan ................... 1-226211

[51] Int. Cl.$^5$ .................... C12N 9/44; C12N 1/00
[52] U.S. Cl. ..................... 435/210; 435/832
[58] Field of Search .................. 435/210, 832

[56] References Cited

U.S. PATENT DOCUMENTS

| | | | |
|---|---|---|---|
| 3,490,995 | 1/1970 | Wallenfels et al. | 435/210 |
| 3,806,419 | 4/1974 | Heady | 435/210 |
| 3,963,575 | 6/1976 | Balich | 435/210 |
| 4,318,989 | 3/1982 | Marshall | 435/210 |
| 4,612,287 | 9/1986 | Coleman et al. | 435/210 |
| 4,628,028 | 12/1986 | Katkocin et al. | 435/210 |
| 4,628,031 | 12/1986 | Zeikus et al. | 435/210 |
| 4,734,364 | 3/1988 | Line et al. | 435/210 |

FOREIGN PATENT DOCUMENTS

| | | | |
|---|---|---|---|
| 258050 | 3/1988 | European Pat. Off. | 435/210 |
| 60-186282 | 9/1985 | Japan | 435/210 |
| 63-36780 | 2/1988 | Japan | 435/210 |
| 63-42696 | 2/1988 | Japan | 435/210 |

OTHER PUBLICATIONS

Biochimica et Biophysica Acta, vol. 397, 1975, pp. 188-193, Elsevier Scientific Pub. Co., Amsterdam, NL; N. Nakamura et al.: "Purification and some properties of alkaline pullulanase from a strain of bacillus No. 202-1, an alkalophilic microorganism".

Fems Microbiology, vol. 20, 1983, pp. 55-59, Elsevier; C. T. Kelly et al.: "Extracellular alpha-glucosidase of an alkalophilic microorganism, Bacillus sp. ATCC 21591".

Wallenfels, *Pullulanase* from Aerobactic . . . BBRC, 1966, pp. 254-261.

*Primary Examiner*—David M. Naff
*Assistant Examiner*—Mike Meller
*Attorney, Agent, or Firm*—Oblon, Spivak, McClelland, Maier & Neustadt

[57] ABSTRACT

A novel alkaline pullulanase; a microorganism producing the alkaline pullulanase; and a process for producing the alkaline pullulanase are disclosed. The alkaline pullulanase of the present invention has a higher optimum pH range (pH 9.5-11) than conventional alkaline pullulanases and shows excellent stability in a wider pH range. It has also an optimum temperature of higher than 50° C. and is thermally stable up to 40° C. The alkaline pullulanase has also strong reistance to almost all detergent components such as surfactants, chelating agents, proteases for detergents, and the like. The alkaline pullulanase can advantageously be used as a detergent component. Also, it can be utilized for producing many kinds of oligosaccharides and also together with α-amylase for producing various monosaccharides.

2 Claims, 5 Drawing Sheets 5,147,795

ALKALINE PULLULANASE FROM BACILLUS SP. FERM P-10887

BACKGROUND OF THE INVENTION

Field of the Invention

This invention relates to a novel alkaline pullulanase, a microorganism producing the alkaline pullulanase, and a process for producing the alkaline pullulanase.

Description of the Background Art

Pullulanase is an enzyme which hydrolyzes only α-1,6-glycosidic linkage of pullulan and finally produces maltotriose. Pullulanase was first discovered from a strain belonging to *Aerobacter aerogenes* by Bender and Wallenfels in 1961 [*Biochem. Z.,* 334, 79, (1961)]. Recently, various microorganisms capable of producing pullulanase have been reported. These microorganisms are, for example, Bacillus sp. [*J. Jpn. Soc. Starch Sci.,* 30, 200, (1983)]; *Bacillus acidopullulyticus* [*Agric. Biol. Chem.,* 52, 2293, (1984)]; *Bacillus stearothermophilus* [*Eur. J. Appl. Microbiol. Biotechnol.,* 17, 24, (1983)]; *Streptococcus mitis* [*Biochem. J.,* 108, 33, (1968)]; and *Lactobacillus* [*Denpun Kagaku,* 28, 72, (1981)].

It is known that pullulanases not only possess the above activity against pullulan, but also hydrolysis activities against α-1,6-glycosidic bond of starch, glycogen, amylopectin, as well as against branched oligosaccharides produced partial decomposition of these compounds. Because of this characteristic, pullulanase is called a "debranching enzyme".

Further, it has been found that pullulanase in combination with both endo-type amylase and exo-type amylase could yield glucose or maltooligo-saccharides such as maltose, maltotriose, maltotetraose, maltopentaose, or maltohexaose from starch in a high yield. This characteristic has lately attracted considerable attention.

There is a report that pullulanase having these characteristics was utilized in combination with amylase as an additive for dish-washing detergents or laundry detergents, thereby remarkably improving detergency mainly against starch soils (Japanese Patent Application No. 285424/1988). Further utilization of pullulanase is expected in these fields.

However, almost all naturally occurring pullulanases are classified into the neutral or acidic pullulanases which exhibit maximum and stable enzymatic activity in neutral or acidic conditions. There are few alkaline or alkali-resistant pullulanases having a better stability and exhibiting the maximum activity at an alkaline pH range at which cloth-washing or dish-washing is performed. An alkaline pullulanase herein denotes that having its optimum pH at an alkaline range. An alkali-resistant pullulanase denotes that having its optimum pH in a neutral to acidic range, but having a sufficient degree of activities in an alkaline range as it has at its optimum pH while retaining a good stability. The word "neutral" herein designates a pH range of 6-8 and the word "alkaline" designates a pH range of not less than 8.

No process for producing alkaline pullulanases nor alkali-resistant pullulanases is heretofore known, except for a report of Horikoshi et al., which discloses a process for producing alkali pullulanase by culturing an alkalophilic microorganism belonging to genus Bacillus *Biochem. Biophys. Acta,* 397, 188, (1975), and Japanese Patent Publication No. 27786/1978).

The pullulanase of Horikoshi et al. is an enzyme having its optimum pH at an alkaline range and possessing a wider substrate specificity than conventionally known pullulanases. However, since its optimum pH is in a weak alkaline range of 8-9, it is not applicable to detergent compositions. In addition, the process of Horikoshi et al. has a disadvantage of low productivity of enzyme. This type of process is therefore unsuitable for industrial fermentative production. Because of these reasons, the development of pullulanases having an optimum pH in higher alkaline range has been desired.

Dish-washing or cloth-washing is usually carried out in a wide pH range of from neutral to high alkaline range. It is therefore worthwhile to discover and obtain natural microorganisms producing pullulanases having an optimum pH at highly alkaline range and usable for dish-washing and cloth-washing detergents.

In view of this situation, the present inventors have carried out extensive studies in order to obtain natural microorganisms capable of producing alkaline pullulanase, and, as a result, found that a novel alkaline pullulanase having an optimum pH in a high alkaline range of from 9.5 to 11 could be obtained by culturing a specific microorganism belonging to genus Bacillus. This finding has led to the completion of the present invention.

SUMMARY OF THE INVENTION

Accordingly, an object of this invention is to provide a novel alkaline pullulanase possessing the following enzymological characteristics:

(1) Action

Hydrolyzes the α-1,6-linkage of pullulan to produce maltotriose, and hydrolyzes α-1,6 glycosidic bond of starch, amylopectin, glycogen, or their partial decomposition products.

(2) Working pH and optimum pH range

Has an active pH range of 4-12 with an optimum pH range being 9.5-11.

(3) pH stability

Is stable in a pH range of 7-10 and retains relative activity of 50% or more of the activity at the optimum pH range even in a pH range of 6-11.5, when treated at 45° C. for 10 minutes.

(4) Working temperature and optimum temperature

Is active at a wide temperature range of from 10° to 60° C. with an optimum temperature being around 55° C.

(5) Thermal stability

Is very stable up to 45° C., when treated in 10 mM glycine-NaCl—NaOH buffer (pH 9.5) for 30 minutes.

(6) Molecular weight

About 110,000±10,000, when measured by means of a gel filtration method using Bio-gel A 0.5 m.

Another object of the present invention is to provide a novel purified alkaline pullulanase Z-1 possessing the following enzymological characteristics:

(1) Action

Hydrolyzes α-1,6-linkage of pullulan to produces maltotriose, and hydrolyzes α-1,6 glycosidic bond of starch, amylopectin, glycogen, or their partial decomposition products.

(2) Substrate specificity

Possesses hydrolytic activity against α-1,6-glycosidic bond of sugars having a greater polymerization degree than that of maltose.

(3) Working pH and optimum pH range

Has an active pH range of 5-11 with an optimum pH range being 9.5-11.

(4) pH stability

Is stable in a pH range of 8-10 and retains relative activity of 50% or more of the activity at the optimum pH range even in a pH range of 7-10.5, when treated at 45° C. for 10 minutes.

(5) Working temperature and optimum temperature

Is active at a wide temperature range of from 10° to 60° C. with an optimum temperature being around 50° C.

(6) Thermal stability

Is very stable at 40° C. when treated in 10 mM glycine-NaCl-NaOH buffer (pH 9.5) for 30 minutes.

(7) Molecular weight

About 120,000±5,000, when measured by means of electrophoresis using sodium dodecylsulfate.

(8) Effects of metal ions

Adversely affected $Hg^{2+}$, $Cd^{2+}$, $Mn^{2+}$, and $Pb^{2+}$ ions.

(9) Effects of detergents

Scarcely affected by surfactants such as linear alkylbenzene sulfonate (LAS), sodium alkyl sulfate (AS), sodium polyoxyethylene alkyl sulfate (ES), sodium α-olefin sulfonate (AOS), sodium α-sulfonated fatty acid ester (α-SFE), sodium alkyl sulfonate (SAS), sodium dodecyl sulfate (SDS), soaps and softanol.

(10) Effects of chelating agents

Scarcely affected by EDTA, EGTA, citric acid, and zeolite.

(11) Resistance to protease

Exhibits strong resistance to alkaline proteases.

Still another object of the present invention is to provide a microorganism belonging to genus Bacillus and capable of producing the alkaline pullulanase having the above characteristics.

Further object of the present invention is to provide a process for producing the alkaline pullulanase having the above characteristics.

Other objects, features and advantages of the invention will hereinafter become more readily apparent from the following description.

DETAILED DESCRIPTION OF THE INVENTION AND PREFERRED EMBODIMENTS

Figure 1:
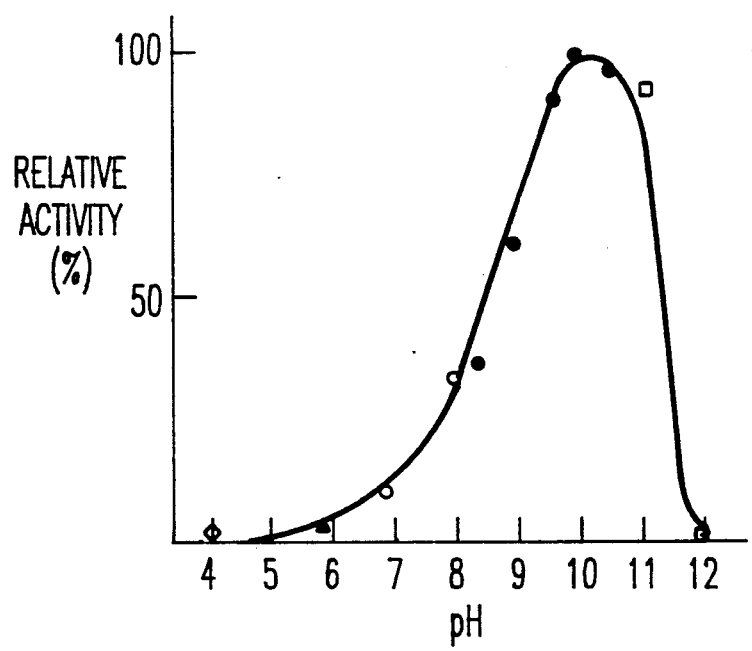
FIG. 1 is a drawing showing the relation of relative activity vs. reaction pH of the alkaline pullulanase of this invention.

There are no restrictions as to the microorganisms of the present invention inasmuch as they belong to genus Bacillus and are capable of producing pullulanase having an optimum pH at 9.5-11. As a typical example, an alkalophilic microorganism, Bacillus sp. KSM-AP1876 which was discovered by the inventors in the soils in Yokahama-shi, Kanagawa-ken, Japan is given.

Mycological characteristics of Bacillus sp. KSM-AP1876 which is one of the microorganisms of this invention is now discussed. The following culture media of 21 sorts (Media 1 to 21) are used for the classification of strain. They all contain 0.5% by weight of sterilized sodium carbonate ($Na_2CO_3$). Compositions of the culture media used (% by weight)

Medium 1: nutrient broth, 0.8; agar powder (manufactured by Wako Pure Chemical Co.), 1.5

Medium 2: nutrient broth, 0.8

Medium 3: nutrient broth, 0.8; gelatin, 20.0; agar powder (manufactured by Wako Pure Chemical), 1.5

Medium 4: Bacto litmus milk, 10.5

Medium 5: nutrient broth, 0.8; $KNO_3$, 0.1

Medium 6: Bacto peptone, 0.7; NaCl, 0.5; glucose, 0.5

Medium 7: SIM agar medium (manufactured by Eiken Kagaku), an amount indicated

Medium 8: TSI agar (manufactured by Eiken Kagaku), an amount indicated

Medium 9: yeast extract, 0.5; Bacto peptone, 1.5; $K_2HPO_4$, 0.1; $MgSO_4.7H_2O$, 0.02; soluble starch, 2.0; agar powder (manufactured by Wako Pure Chemical), 1.5

Medium 10: Koser's medium (manufactured by Eiken Kagaku), an amount indicated

Medium 11: Christensen's medium (manufactured by Eiken Kagaku), an amount indicated Medium 12: the medium including the following compositions (1) and (2) to which added are nitrogen sources consisting of sodium nitrate, sodium nitrite, ammonium chloride, and ammonium phosphate in an amount of 0.25%, 0.2025%, 0.158%, and 0.195% by weight respectively in the medium.

(1) yeast extract, 0.05; $Na_2SO_4$, 0.1; $KH_2PO_4$, 0.1; glucose, 1.0

(2) yeast extract, 0.05; $Na_2SO_4$, 0.1; $KH_2PO_4$, 0.1; glucose, 1.0; $CaCl_2.2H_2O$, 0.05; $MnSO_4.4-6H_2O$, 0.01; $FeSO_4.7H_2O$, 0.001; $MgSO_4.7H_2O$, 0.02

Medium 13: King A medium "Eiken" (manufactured by Eiken Kagaku), an amount indicated Medium 14: King B medium "Eiken" (manufactured by Eiken Kagaku), an amount indicated Medium 15: urea medium "Eiken" (manufactured by Eiken Kagaku), an amount indicated Medium 16: cytochrome-oxidase test filter paper (manufactured by Nissui Pharmaceutical Co., Ltd.)

Medium 17: 3% aqueous hydrogen peroxide

Medium 18: Bacto peptone, 0.5; yeast extract, 0.5; $K_2HPO_4$, 0.1; glucose, 1.0; $MgSO_4.7H_2O$, 0.02

Medium 19: Bacto peptone, 2.7; NaCl, 5.5; $K_2HPO_4$, 0.3; glucose, 0.5; bromthymol blue, 0.06; agar powder (manufactured by Wako Pure Chemical), 1.5

Medium 20: $(NH_4)_2HPO_4$, 0.1; KCl, 0.02; $MgSO_4 \cdot 7H_2O$, 0.02; yeast extract, 0.05; sugar, 1.0

Medium 21: casein, 0.5; yeast extract, 0.5; glucose, 1.0; $K_2HPO_4$, 0.1; $MgSO_4 \cdot 7H_2O$, 0.02; agar powder (manufactured by Wako Pure Chemical), 1.5

Mycological characteristics (1) Observation under microscope

Cells are rods of a size of 1.0-2.2 $\mu m \times$ 2.2-4.4 $\mu m$, with an elliptical endospore (0.8-1.0 $\mu m \times$ 1.0-1.8 $\mu m$) forming at their subterminals. They have flagella and are motile. Gram's staining is positive. Acid fastness: Negative (2) Growth in various culture media (a) Nutrient broth-agar plate (Medium 1)

Growth of cells is good. Colony has a circular shape, with its surface being smooth and its peripheral end being smooth or wavy. The color of the colony is milky, semitransparent, and glossy.

(b) Nutrient broth-agar slant culture (Medium 1)

Cells can grow. Colony has a cloth-spreading shape, with a color of the colony being glossy milky, and semitransparent.

(c) Liquid nutrient broth (Medium 2)

Cells can grow.

(d) Stab culturing in nutrient broth-gelatin (Medium 3)

Growth of cells is good. Liquefaction of gelatin is observed.

(e) Litmus milk medium (Medium 4)

Milk coagulation and peptonization are not observed. Litmus discoloration is indeterminable because the medium is an alkaline medium.

(3) Physiological characteristics (a) Nitrate reduction and denitrification (Medium 5)

Nitrate reduction: positive

Denitrification: negative (b) MR test (Medium 6)

Indeterminable because the medium is an alkaline medium.

(c) V-P test (Medium 6)

Negative (d) Production of indole (Medium 7)

Negative (e) Production of hydrogen sulfide (Medium 8)

Negative (f) Hydrolysis of starch (Medium 9)

Positive (g) Utilization of citric acid (Medium 10, Medium 11)

Negative in Koser's medium (Medium 10) and indeterminable in Christensen's medium (Medium 11)

(h) Utilization of inorganic nitrogen sources (Medium 12)

Nitrate, nitrite, and ammonium salts are all utilized.

(i) Discoloration (Medium 13, Medium 14)

Negative (j) Urease (Medium 15)

Negative (k) Oxidase (Medium 16)

Indeterminable (l) Catalase (Medium 17)

Positive (m) Growth range (Medium 18)

Growth temperature: 20°-40° C.,

Optimum growth temperature: 30°-35° C.

Growth pH range: 7-10.5

Optimum pH: 10

(n) Behavior on oxygen

Aerobic (o) O-F test (Medium 19)

Indeterminable because the medium is an alkaline medium. Cells can grow only in an aerobic condition.

(p) Sugar utilization (Medium 20)

The following sugars are utilized:

L-arabinose, D-xylose, D-glucose, D-mannose, D-fructose, D-galactose, maltose, sucrose, lactose, trehalose, D-sorbitol, D-mannitol, glycerol, starch, salicin, D-ribose, and dextrin.

(q) Growth in a medium containing sodium salt (a modification of Medium 1)

Cells can grow in the presence of a 5% of sodium chloride, but can not grow in the presence of a 7% sodium chloride.

(r) Hydrolysis of casein (Medium 21)

Positive

Based on the above mycological characteristics, the strains of the present invention were examined referring to Bergey's Manual of Determinative Bacteriology, Vol. 8 and "The Genus Bacillus" Ruth, E. Gordon, Agriculture Handbook No. 427, Agricultural Research Service, U.S. Department of Agriculture Washington D.C., (1973), and determined as a microorganism belonging to genus Bacillus, ascospore rods. The strain does not grow in a neutral range, but can grow mostly in a highly alkaline range. From this fact, the strain of the present invention is classified as an alkalophilic microorganism which was demonstrated by Horikoshi and Akiba, "Alkalophilic Microorganism", Japan Scientific Society Press (Tokyo), 1982. The strain of the present invention is distinguished from a group of microorganisms belonging to genus Bacillus which grow in an neutral range.

The strain of the present invention, other than the above characteristics, have mycologically different characteristics from those of any conventionally known alkalophilic Bacillus. Accordingly, the strain of the present invention was determined as a novel strain and named Bacillus sp. KSM-AP1876, which was deposited with Fermentation Research Institute, Agency of Industrial Science and Technology as FERM P-10887.

The production of alkaline pullulanase of the present invention can be processed by inoculating the microorganisms of the present invention and culturing the microorganisms according to conventional culturing methods. Inclusion of a suitable amount of carbon and nitrogen sources which the microorganism can utilize in the medium is desirable. There are no specific limitations as to the carbon and nitrogen sources. Enumerated as nitrogen sources are organic nitrogen sources such as corn gluten meal, soybean flour, corn steep liquor, casamino acid, yeast extract, pharma media, meat extract, tryptone, soytone, hypro, ajipower, soybean meal, cotton seed meal, cultivator, ajipron, zest, and the like; and inorganic nitrogen sources such as ammonium sulfate, ammonium nitrate, ammonium phosphate, ammonium carbonate, sodium nitrate, ammonium acetate, and the like. Given as examples of carbon sources are soluble starch, insoluble starch, amylopectin, glycogen, pullulan, and branched oligomers produced by their partial decomposition, and utilizable carbon sources are such as glucose, maltose, arabinose, xylose, ribose, mannose, fructose, galactose, sucrose, lactose, trehalose, mannitol, sorbitol, glycerol, and utilizable organic acids are such as acetic acid and the like. In addition to these carbon and nitrogen sources, inorganic ions such as phosphates, magnesium, calcium, manganese, zinc, cobalt, sodium, potassium, and the like, as required, other organic or inorganic micronutrients can be added into the culture medium.

Alkaline pullulanase of the present invention can be prepared from the culture broth by means of conventional collection and purification methods adapted to general enzymes. Specifically, cells are separated from the culture broth by means of conventional solid-liquid separation methods, such as, centrifugation, filtration, or the like, to obtain a crude enzyme liquid. Although it is possible to use the crude enzyme liquid thus obtained as is, they can also be served as a purified enzyme, as required, after separating by means of separation methods, e.g. salting out, precipitation, ultrafiltration, and the like, to obtain crude enzyme, and purifying and crystallizing the crude enzyme by conventional methods. Suitable purifying methods are for example, DEAE cellulose (manufactured by Whatman Co.) adsorption, DEAE cellulose chromatography, Sephacryl (manufactured by Pharmasia Co.) chromatography, DEAE Toyopeal (manufactured by Tosoh) chromatography, and butyl Toyopeal chromatography.

Enzymological characteristics of the novel enzyme, alkaline pullulanase of this invention are now discussed. Enzymatic activities were measured using the following buffer solutions (50 mM each) according to the method explained below.

The buffer solutions:
pH 4-6: acetate buffer
pH 6-8: phosphate buffer
pH 8-11: glycine-NaCl-NaOH buffer
pH 11-12: KCl-NaOH buffer Measurement of enzymatic activity:
0.1 ml of enzyme solution was added to 0.9 ml of each substrate solution prepared from each buffer solution containing pullulan (final concentration in the reaction system: 0.25%, w/v) and the mixture was reacted at 40° C. for 30 minutes. After the reaction, reducing sugars were quantitatively determined by means of the 3,5-dinitro-salicylic acid (DNS) procedure. Specifically, 1.0 ml of DNS reagent was added to 1.0 ml of reaction mixture and the mixture was heated at 100° C. to develop a color. After cooling, 4.0 ml of deionized water was added to the mixture. This was subjected to colorimetric quantitative analysis at a wave length of 535 nm. One unit (1 U) of enzyme activity was defined as the amount of enzyme which released 1 μmol of reducing sugar as glucose per minute under the standard assay conditions.

Enzymological characteristics of crude alkaline pullulanase (1) Action
Hydrolyzes α-1,6-linkage of pullulan to produce maltotriose, and, as shown in Table 1, hydrolyzes α-1,6 glycosidic bond of starch, amylopectin, glycogen, or their partial decomposition products.

TABLE 1

| Substrate | Concentration | Relative Activity (%) |
|---|---|---|
| Pullulan | $1 \times 10^{-5}$ | 100 |
| Glycogen (oyster) | $1 \times 10^{-6}$ | 1 |
| Glycogen (rabbit liver) | $1 \times 10^{-6}$ | 6 |
| Amylopectin | $1 \times 10^{-8}$ | 55 |

(2) Working pH and optimum pH range
Has an active pH range of 4-12 with an optimum pH range being 9.5-11 and retains relative activity of 50% or more of the activity at the optimum pH range even in a pH range of 8.5-11.5.

Pullulanase activities at various pH were measured using each reaction system consisting of 0.25% (w/v) of pullulan and a buffer solution of 10 mM acetate (pH 4-6), phosphate (pH 7-8), glycine-NaCl—NaOH (pH 8.5-10.5), or KCl-NaOH (pH 11-12). Each reaction was carried out at 40° C. for 30 minutes. The results are shown in FIG. 1.

(3) pH stability
Is stable in a pH range of 7-10 and keeps relative activity of 50% or more of the activity at the optimum pH range even in a pH range of 6-11.5.

Figure 2:
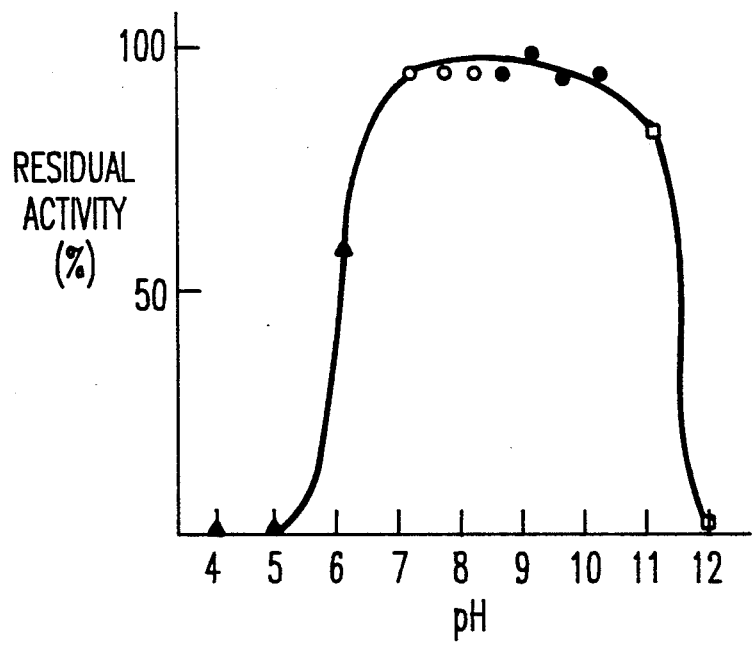
FIG. 2 is a drawing showing the relation of pH vs. residual activity of the alkaline pullulanase of this invention.

Pullulanase activities at various pH were measured using each reaction system consisting of 0.25% (w/v) of pullulan and a buffer solution of 10 mM acetate (pH 4-6), phosphate (pH 7-8), glycine-NaCl—NaOH (pH 8.5-10.5), or KCl—NaOH (pH 11-12). Each reaction was carried out at 45° C. for 10 minutes. The results are shown in FIG. 2.

Figure 3:
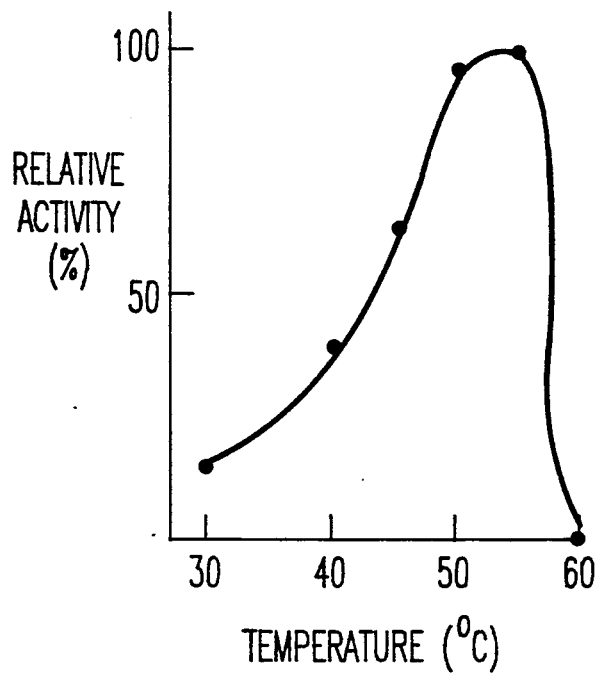
FIG. 3 is a drawing showing the relation of reaction temperature (pH 9.5) vs. relative activity of the alkaline pullulanase of the present invention.

(4) Working temperature and optimum temperature
Acts at a wide temperature range of 10° to 60° C. with an optimum temperature being 55° C. (see FIG. 3).

Figure 4:
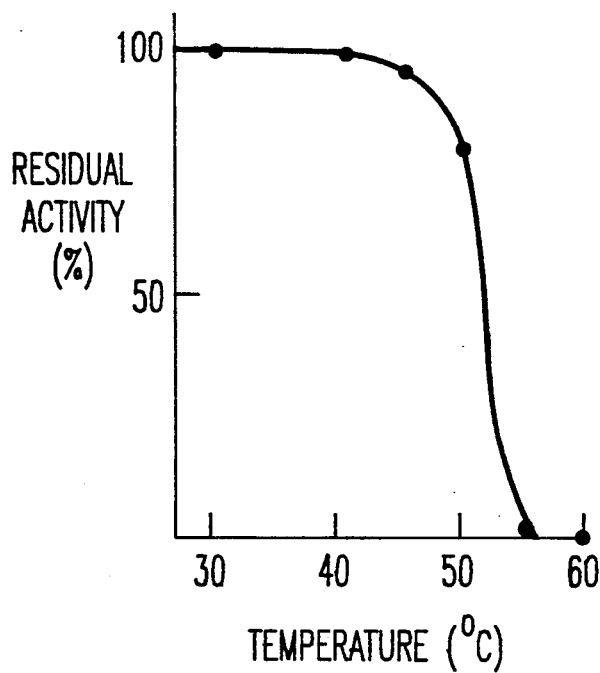
FIG. 4 is a drawing showing the relation of reaction temperature (pH 9.5) vs. residual activity of the alkaline pullulanase of the present invention.

(5) Thermal stability
Residual activities of the enzyme, when heat-treated at various temperatures for 30 minutes in glycine-NaCl—NaOH buffer (pH 9.5), were measured. The enzyme of this invention scarcely loses its activity at 45° C., and has the residual activity of about 50% even at 52° C. (see FIG. 4).

(6) Molecular weight
The molecular weight of the enzyme of the present invention was measured by means of a gel filtration method using Bio-gel A 0.5m. The enzyme of this invention has a molecular weight of approximately 110,000±10,000.

(7) Effects of metal ions
Addition of $Hg^{2+}$, $Pb^{2+}$, and $Cd^{2+}$ ions (1 mM each) gives an adverse effect and addition of $Mn^{2+}$ ion (1 mM) gives a slightly adverse effect.

(8) Effects of detergents
0.05% by weight of surfactants such as linear alkyl benzene sulfonate (LAS), sodium alkyl sulfate (AS), sodium polyoxyethylene alkyl sulfate (ES), sodium α-olefin sulfonate (AOS), sodium α-sulfonated fatty acid ester (α-SFE), sodium alkyl sulfonate (SAS), sodium dodecyl sulfate (SDS), soaps, and softanol was tested at 40° C. for 15 minutes to confirm no adverse effect on enzymatic activities.

(9) Effect of chelating agents
Chelating agents such as EDTA (10 mM), EGTA (10 mM), citric acid (0.05% by weight), and zeolite (0.05% by weight) give no adverse effect on enzymatic activities.

(10) Resistance to protease
In the presence of alkaline protease, for example, API-21 (Showa Denko), Maxatase (IBIS), and Sabinase, Alkalase, and Esperase (Novo) in an amount of 0.2 AU/l, the activities were measured, to confirm that the enzyme of this invention had strong resistance to any proteases.

Enzymological characteristics of purified alkaline pullulanase Z-1

(1) Action

Hydrolyzes α-1,6-linkage of pullulan to produce maltotriose, and hydrolyzes α-1,6 glycosidic bond of starch, amylopectin, glycogen, or their partial decomposition products.

(2) Substrate specificity

Possesses hydrolytic activity against α-1,6-glycosidic bond of sugars having a greater polymerization degree than that of maltose as shown in Table 2.

TABLE 2

| Substrate | Concentration (M) | Relative Activity (%) |
|---|---|---|
| Pullulan | $1 \times 10^{-5}$ | 100 |
| Glycogen (oyster) | $1 \times 10^{-6}$ | 0.2 |
| Glycogen (rabbit liver) | $1 \times 10^{-6}$ | 0.0 |
| Amylopectin | $1 \times 10^{-8}$ | 6.1 |
| Amylose | $1 \times 10^{-8}$ | 0.0 |
| Maltose | $1 \times 10^{-2}$ | 0.0 |
| Maltotriose | $1 \times 10^{-2}$ | 0.0 |
| Panose | $1 \times 10^{-2}$ | 0.0 |
| Isomaltose | $1 \times 10^{-2}$ | 0.0 |
| Isomaltotriose | $1 \times 10^{-2}$ | 0.0 |
| Gentiobiose | $1 \times 10^{-2}$ | 0.0 |

(3) Working pH and optimum pH range

Has an active pH range of 5–11 with an optimum pH range being 9.5–11.

Figure 5:
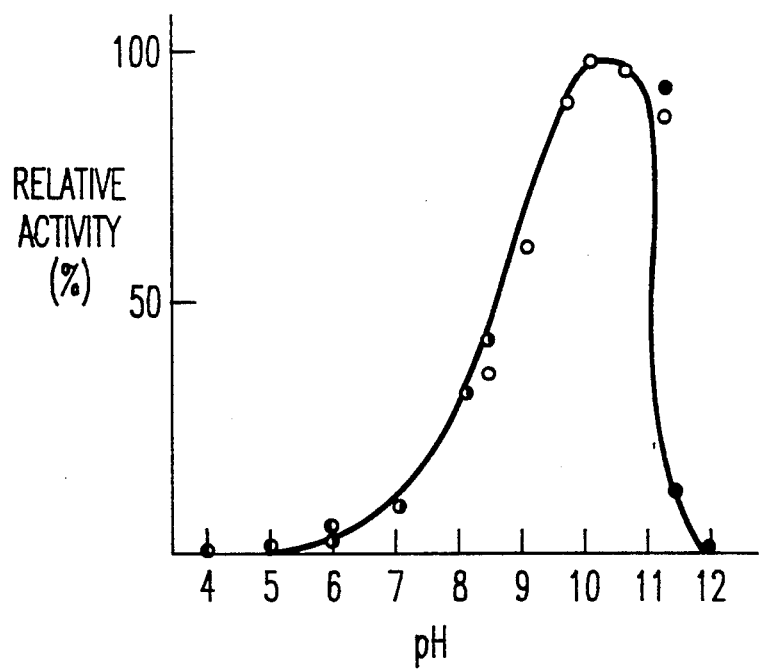
FIG. 5 is a drawing showing the relation of relative activity vs. reaction pH of the alkaline pullulanase Z-1 of this invention.

Pullulanase activities at various pH were measured using each reaction system consisting of 0.25% (w/v) of pullulan and a buffer solution of 10 mM acetate (pH 4–6), phosphate (pH 6–8.5), glycine-NaCl—NaOH (pH 8.5–11), or KCl—NaOH (pH 11–12). Each reaction was carried out at 40° C. for 30 minutes. The results are shown in FIG. 5.

(4) pH stability

Is stable in a pH range of 8–10 and retains relative activity of 50% or more of the activity at the optimum pH range even in a pH range of 7–10.5.

Figure 6:
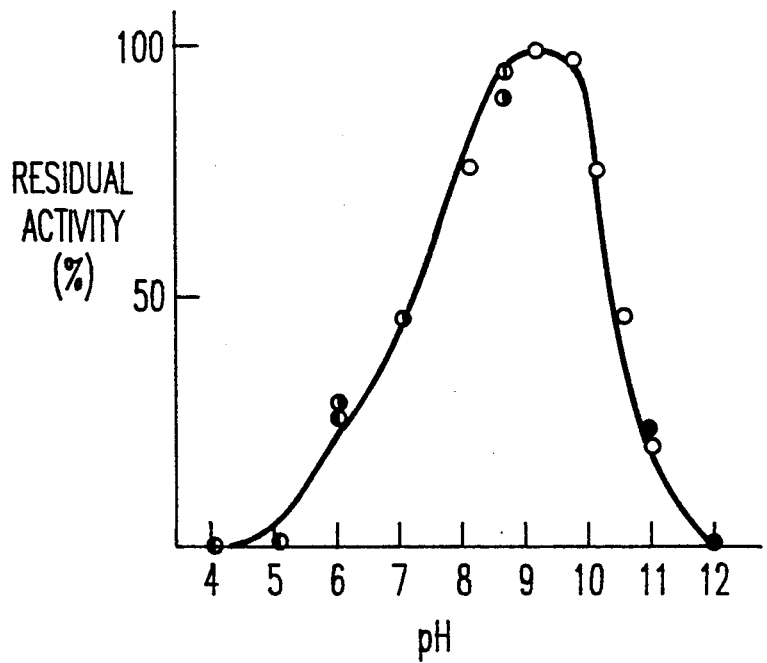
FIG. 6 is a drawing showing the relation of pH vs. residual activity of the alkaline pullulanase Z-1 of this invention.

Pullulanase activities at various pH were measured using each reaction system consisting of 0.25% (w/v) of pullulan and a buffer solution of 10 mM acetate (pH 4–6), phosphate (pH 6–8.5), glycine-NaCl—NaOH (pH 8.5–11), or KCl—NaOH (pH 11–12). Each reaction was carried out at 45° C. for 10 minutes. The results are shown in FIG. 6.

(5) Working temperature and optimum temperature

Figure 7:
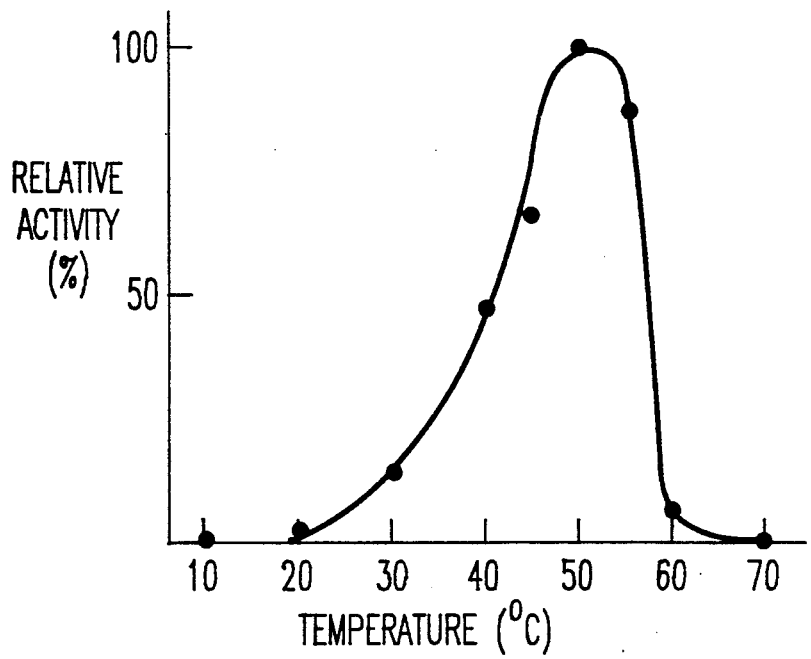
FIG. 7 is a drawing showing the relation of reaction temperature (pH 9.5) vs. relative activity of the alkaline pullulanase Z-1 of the present invention.

Is active at a wide temperature range of from 10° to 60° C. with an optimum temperature being 50° C. (see FIG. 7).

(6) Thermal stability

Figure 8:
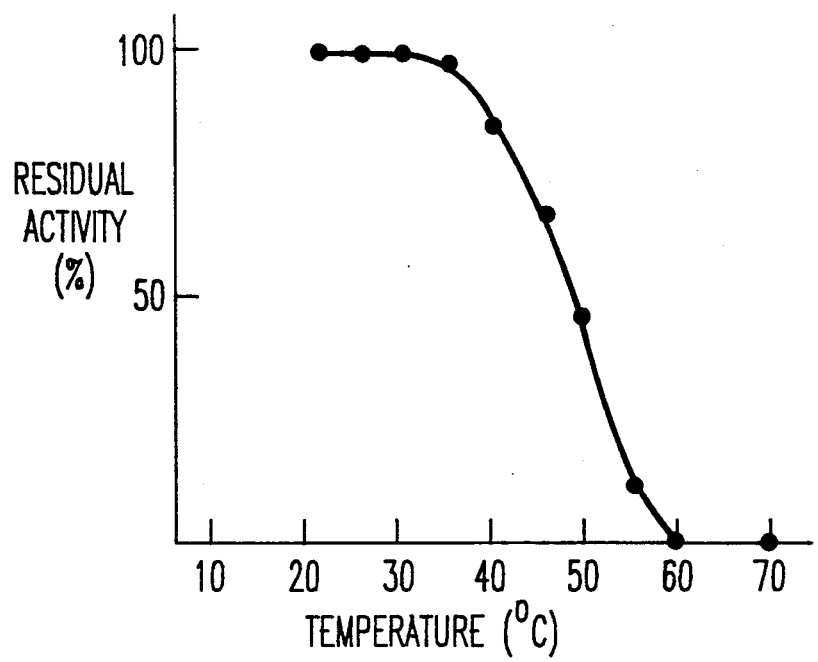
FIG. 8 is a drawing showing the relation of reaction temperature (pH 9.5) vs. residual activity of the alkaline pullulanase Z-1 of the present invention.

Residual activities of the enzyme, when heat-treated at various temperatures for 30 minutes in glycine-NaCl—NaOH buffer (pH 9.5), were measured. The enzyme of this invention scarcely loses its activity at 40° C., and has the residual activity of about 50% even at 50° C. (see FIG. 8).

(7) Molecular weight

The molecular weight of the enzyme of the present invention was measured by means of SDS-polyacrylamide gel electrophoresis (7.5% gel). The enzyme of this invention has a molecular weight of approximately 120,000±5,000.

(8) Effects of metal ions

Addition of $Hg^{2+}$, $Cd^{2+}$, and $Mn^{2+}$ ions (1 mM each) gives an adverse effect and addition of $Pb^{2+}$ ion (1 mM) gives a slightly adverse effect.

(9) Effects of detergents 0.05% by weight of surfactants such as linear alkyl benzene sulfonate (LAS), sodium alkyl sulfate (AS), sodium polyoxyethylene alkyl sulfate (ES), sodium α-olefin sulfonate (AOS), sodium α-sulfonated fatty acid ester (α-SFE), sodium alkyl sulfonate (SAS), sodium dodecyl sulfate (SDS), soaps, and softanol was tested at 40° C. for 15 minutes to confirm no adverse effect on enzymatic activities.

(10) Effects of chelating agents

Chelating agents such as EDTA (10 mM), EGTA (10 mM), citric acid (0.05% by weight), and zeolite (0.05% by weight) give no adverse effect on enzymatic activities.

(11) Resistance to protease

In the presence of alkaline protease, for example, API-21 (Showa Denko), Maxatase (IBIS), Sabinase, Alkalase, and Esperase (Novo) in an amount of 0.2 AU/l, the activities were measured, to confirm that the enzyme of this invention had strong resistance to any proteases.

Alkaline pullulanase of the present invention has a higher optimum pH range (pH 9.5–11) than conventional alkaline pullulanases and shows excellent stability in a wider pH range. It has an optimum temperature of higher than 50° C. and is thermally stable up to 40° C. Further, alkaline pullulanase of the present invention has strong resistance to almost all detergent components such as surfactants, chelating agents, protease for detergents, and the like. Accordingly, the enzyme of the present invention can advantageously be used as a detergent component. In addition, the enzyme of the present invention can be utilized for producing many kind of oligosaccharides and also together with α-amylase for producing various monosaccharides. The enzyme of the present invention has thus an outstanding significance in industrial fields.

Other features of the invention will become apparent in the course of the following description of the exemplary embodiments which are given for illustration of the invention and are not intended to be limiting thereof.

EXAMPLES

Example 1

A spoonful of soil (about 0.5 g) of Yokohama-shi, Kanagawa-ken, Japan was suspended in sterilized saline and the mixture was heat-treated at 80° C. for 15 minutes. A supernatant of the heat-treated mixture was appropriately diluted, applied onto an isolating agar medium (Medium A), and cultured at 30° C. for 3 days to grow colonies. The colonies which formed transparent zones in their peripheries due to pullulan dissolution were collected to obtain pullulanase-producing strains. These strains were inoculated into the liquid medium B and shake-cultured at 30° C. for 3 days. After cultivations, the cultured broth was centrifuged to separate a supernatant. The pullulanase activity of the supernatant was measured at pH 10 to select alkaline pullulanase-producing strains. Bacillus sp. KSM-AP1876 (FERM P 10887) were thus obtained.

| | | % by weight |
|---|---|---|
| Medium A | Pullulan | 0.8 |
| | Colored pullulan | 0.2 |
| | Polypeptone | 0.2 |
| | Yeast extract | 0.1 |
| | $KH_2PO_4$ | 0.03 |
| | $(NH_4)_2SO_4$ | 0.1 |
| | $MgSO_4.7H_2O$ | 0.02 |
| | $CaCl_2.2H_2O$ | 0.02 |
| | $FeSO_4.7H_2O$ | 0.001 |

-continued

|  |  | % by weight |
|---|---|---|
|  | MnCl$_2$.4H$_2$O | 0.0001 |
|  | Agar | 1.5 |
|  | Na$_2$CO$_3$ | 0.5 |
|  | pH: 10.0 |  |
| Medium B | Pullulan | 1.0 |
|  | Tryptone | 0.2 |
|  | Yeast extract | 0.1 |
|  | KH$_2$PO$_4$ | 0.03 |
|  | (NH$_4$)$_2$SO$_4$ | 0.1 |
|  | MgSO$_4$.7H$_2$O | 0.02 |
|  | CaCl$_2$.2H$_2$O | 0.02 |
|  | FeSO$_4$.7H$_2$O | 0.001 |
|  | MnCl$_2$.4H$_2$O | 0.0001 |
|  | Na$_2$CO$_3$ | 0.5 |
|  | pH: 10.0 |  |

Example 2

Alkaline pullulanase-producing strains Bacillus sp. KSM-AP1876 was inoculated into the liquid medium B of Example 1 and shake-cultured at 30° C. for 3 days. After cultivation, cells were removed by means of centrifugation to obtain the preparation of crude pullulanase. The crude enzyme was processed according to a conventional method to prepare ethanol-dry powder. As a result, the production of enzyme pullulanase was confirmed as shown in Table 3. The enzymatic activity was measured at pH 9.

TABLE 3

| Strain | Amount of enzyme per 1 of medium (g) | Enzymatic activity (U/g) |
|---|---|---|
| KSM-AP1876 | 0.2 | 1,870 |

Example 3

Alkaline pullulanase-producing strains Bacillus sp. KSM-AP1876 was inoculated into a medium which had the same composition as the liquid medium B in Example 1 except that 1% of maltose was added instead of pullulan and shake-cultured at 30° C. for 2-3 days. The pullulanase activity of a supernatant after centrifugation was measured and found to be 211 U per one litter of culture broth.

Example 4

Figure 9:
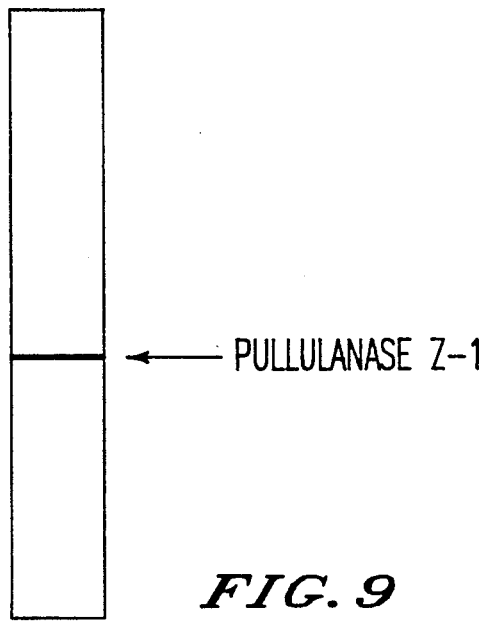
FIG. 9 is a drawing showing the results of electrophoresis of the alkaline pullulanase Z-1 of the present invention.
Figure 10:
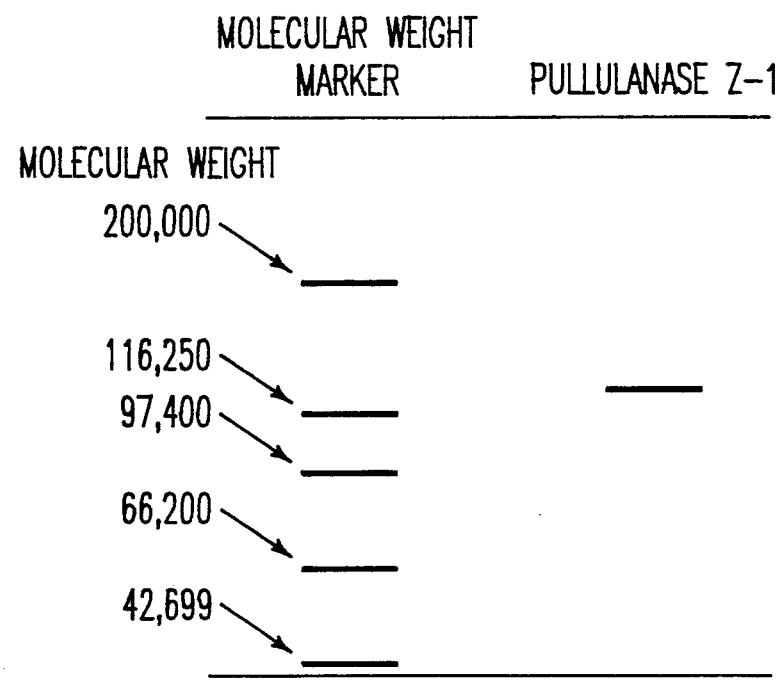
FIG. 10 is a drawing showing the results of SDS electrophoresis of the alkaline pullulanase Z-1 of the present invention.

To the crude enzyme prepared in Example 2 was added DEAE cellulose powder, and pullulanase in the crude enzyme was completely adsorbed to the DEAE cellulose. After 10 mM Tris-HCl buffer (pH 8) was used to wash a resin, enzyme was eluted using 10 mM Tris-HCl buffer (pH 8) containing 0.6M sodium chloride. The 10 mM Tris-HCl buffer in which the enzyme was eluted was subjected to dialysis to concentrate the buffer. Then, the enzyme was adsorbed to DEAE-cellulose DE52 equilibrated with the buffer and gradiently eluted with 10 mM Tris-HCl buffer (pH 8) containing sodium chloride having a concentration of 0-1M to collect active fractions. The active fractions were concentrated using an ultrafiltration membrane (10-kDa cutoff) and dialyzed overnight against 10 mM Tris-HCl buffer (pH 8) containing 0.1M sodium chloride. After having been concentrated and dialyzed, the eluate was subjected to adsorption using a Sephacryl S-200 column equilibrated with 10 mM Tris-HCl buffer (pH 8) containing 0.1M sodium chloride. The enzyme was eluted with 0.1M sodium chloride in 10 mM Tris-HCl buffer to collect active fractions, which were subjected adsorption process using DEAE Toyopeal 650S column. The enzyme adsorbed was gradiently eluted using 10 mM tris-HCl buffer (pH 8) containing sodium chloride having a concentration of 0-1M to collect active fractions. After concentrating on an ultrafiltration membrane, the active fractions were subjected to adsorption process using a Butyl-Toyopeal 650S column equilibrated with 10 mM Tris-HCl buffer containing 2M ammonium sulfate. The column was gradiently eluted with 10 mM Tris-HCl buffer (pH 8) containing ammonium sulfate having a concentration of 2-0M to collect active fractions. The active fractions were concentrated on an ultrafiltration membrane and dialyzed overnight against 10 mM Tris-HCl buffer (pH 8) to obtain a purified enzyme of alkaline pullulanase Z-1. The purified enzyme was subjected to polyacrylamide gel electrophoresis (gel concentration: 15%), according to the method of Davis [Davis D. J., Ann. N.Y. Acad. Sci., 121, 404, (1964)], and stained with Coomassie Brilliant Blue to confirm that it gave a single band (see FIG. 9). The yield of the active enzyme was 4% approximately.

Example 5

The alkaline pullulanase Z-1 obtained in Example 4 was subjected to SDS electrophoresis according to a conventional method to confirm that the enzyme had a molecular weight of 120,000±5,000.

Obviously, numerous modifications and variations of the present invention are possible in light of the above teachings. It is therefore to be understood that the scope of the appended claims, the invention may be practiced otherwise than as specifically described herein.

We claim:

1. A substantially purified alkaline pullulanase derived from Bacillus sp. B2C FERM P-10887 possessing the following enzymological characteristics:
   (a) Action
      Hydrolyzes α-1,6-linkage of pullulan to produce maltotriose, and hydrolyzes α-1,6 glycosidic bond of starch, amylopectin, glycogen, or their partial decomposition products;
   (b) Working pH and optimum pH range
      Has an active pH range of 4-12 with an optimum pH range being 9.5-11;
   (c) pH stability
      Is stable in a pH range of 7-10 when treated at 45° C. for 10 minutes, and retains relative activity of 50% or more in a pH range of 6-11.5 when treated at 45° C. for 10 minutes;
   (d) Working temperature and optimum temperature
      Is active at a wide temperature range of from 10° to 60° C. with an optimum temperature being around 55° C.;
   (e) Thermal stability
      Is very stable up to 45° C., when treated in 10 mM glycine-NaCl—NaOH buffer (pH 9.5) for 30 minutes;
   (f) Molecular weight
      About 110,000±10,000, when measured by means of a gel filtration method using Bio-gel A 0.5 m.

2. A substantially purified alkaline pullulanase Z-1 derived from Bacillus sp. FERM P-10887 possessing the following enzymological characteristics:

(a) Action

Hydrolyzes α-1,6-linkage of pullulan to produce maltotriose, and hydrolyzes α-1,6 glycosidic bond of starch, amylopectin, glycogen, or their partial decomposition products;

(b) Substrate specificity

Possesses hydrolytic activity against α-1,6-glycosidic bond of sugars having a greater polymerization degree than that of maltose;

(c) Working pH and optimum pH range

Has an active pH range of 5–11 with an optimum pH range being 9.5–11;

(d) pH stability

Is stable in a pH range of 8–10 when treated at 45° C. for 10 minutes, and retains relative activity of 50% or more in a pH range of 7–10.5 when treated at 45° C. for 10 minutes;

(e) Working temperature and optimum temperature

Is active at a wide temperature range of from 10° to 60° C. with an optimum temperature being around 50° C.;

(f) Thermal stability

Is very stable up to 40° C., when treated in 10 mM glycine-NaCl—NaOH buffer (pH 9.5) for 30 minutes;

(g) Molecular weight

About 120,000±5,000, when measured by means of electrophoresis using sodium dodecylsulfate;

(h) Effects of metal ions

Is adversely affected by $Hg^{2+}$, $Cd^{2+}$, $Mn^{2+}$, and $Pb^{2+}$ ions.

(i) Effects of detergents

Scarcely affected by surfactants such as LAS, AS, ES, AOS, α-SFE, SAS, SDS, soaps and softanol;

(j) Effect of chelating agents

Scarcely affected by EDTA, EGTA, citric acid, and zeolite;

(k) Resistance to protease

Exhibits strong resistance to alkaline proteases.

* * * * *